United States Patent
Hempel

(10) Patent No.: US 7,436,927 B2
(45) Date of Patent: Oct. 14, 2008

(54) IMAGING APPARATUS AND METHOD FOR THE OPERATION THEREOF

(75) Inventor: Eckhard Hempel, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/622,541

(22) Filed: Jan. 12, 2007

(65) Prior Publication Data

US 2007/0172102 A1  Jul. 26, 2007

(30) Foreign Application Priority Data

Jan. 13, 2006 (DE) .................. 10 2006 001 850

(51) Int. Cl.
*G01N 23/04* (2006.01)
*H05G 1/64* (2006.01)

(52) U.S. Cl. .................... 378/63; 378/62; 378/98.8

(58) Field of Classification Search ............ 378/62–64, 378/205–208; 424/9.3; 600/414, 424; 382/128
See application file for complete search history.

(56) References Cited

U.S. PATENT DOCUMENTS

| | | | |
|---|---|---|---|
| 6,272,204 B1 * | 8/2001 | Amtower et al. | 378/63 |
| 6,435,717 B1 * | 8/2002 | Kohler et al. | 378/206 |
| 6,574,296 B2 * | 6/2003 | Stierstorfer | 378/15 |
| 7,286,632 B2 * | 10/2007 | Yang et al. | 378/37 |
| 2004/0081341 A1 | 4/2004 | Cherek et al. | |
| 2005/0025706 A1 | 2/2005 | Kagermeier | |
| 2005/0049483 A1 | 3/2005 | Vorbuchner | |

\* cited by examiner

*Primary Examiner*—Irakli Kiknadze
(74) *Attorney, Agent, or Firm*—Schiff Hardin LLP

(57) ABSTRACT

An imaging apparatus has an examination space in which a region of an examination subject to be examined can be positioned as well as an optical image acquisition sensor, which is provided to acquire a surface of the examination subject in the examination space and which is linked with an evaluation unit such that acquired surface data are provided as control information for controlling an image acquisition unit, in particular an x-ray device.

15 Claims, 2 Drawing Sheets

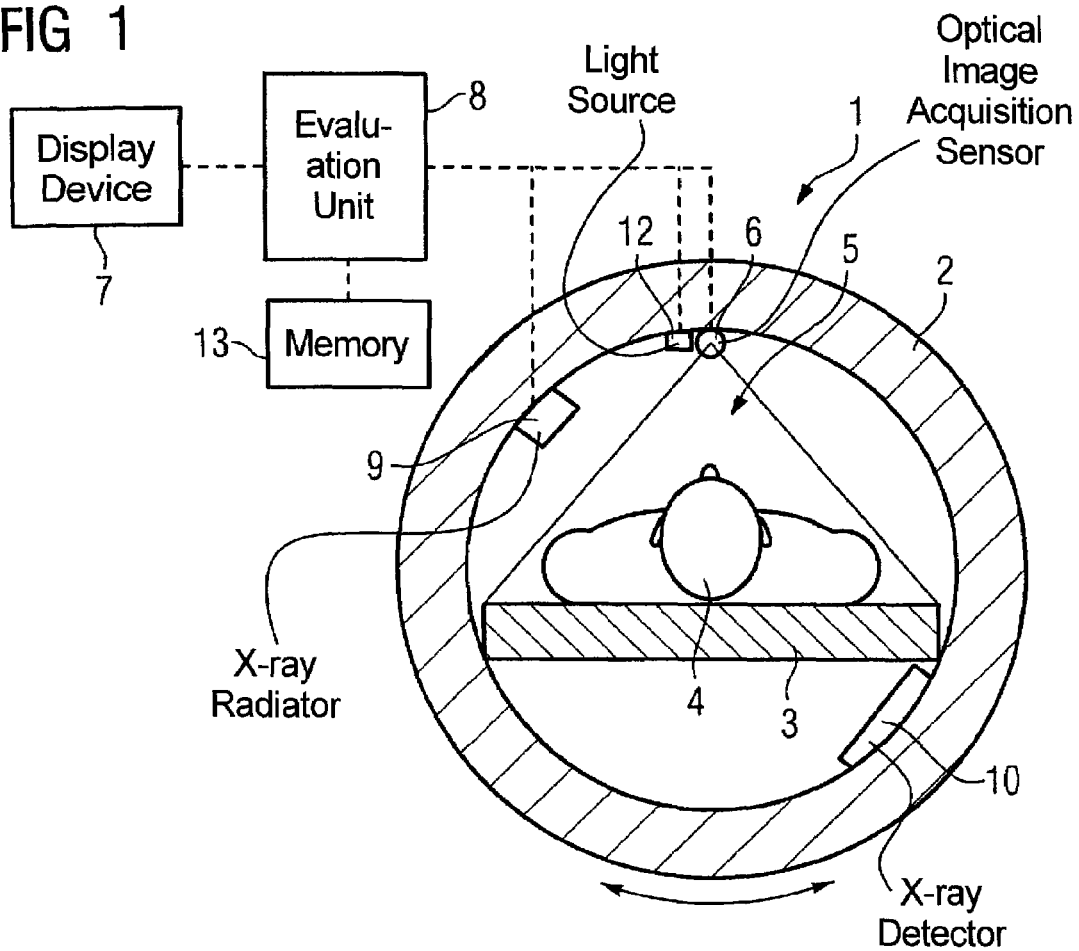
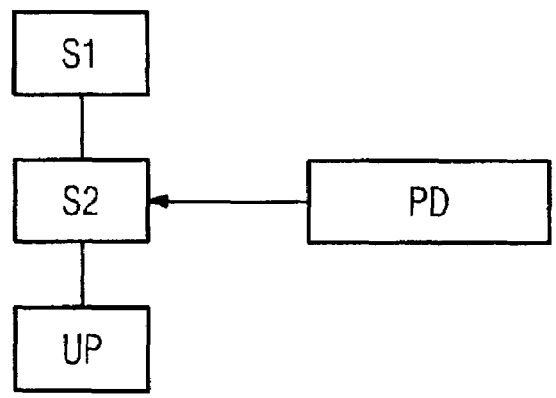

IMAGING APPARATUS AND METHOD FOR THE OPERATION THEREOF

BACKGROUND OF THE INVENTION

1. Field of the Invention

The present invention concerns an imaging apparatus suitable for medical or industrial purposes, in particular an apparatus operating with x-ray radiation or using magnetic resonance, as well as a method for adjustment of operating parameters of such an apparatus.

2. Description of the Prior Art

An imaging apparatus as well as a method of the above general type are described in DE 102 32 676 A1.

In the operation of imaging apparatuses that are provided for medical diagnostic or therapeutic purposes, the significance of the acquired diagnostic data and the therapeutic success generally require the patient to be positioned in an exactly-defined manner relative to the data requisition portion of the apparatus. A device for positioning a patient for this purpose is known, for example, known from DE 103 40 002 B3.

If a patient is examined by computed tomography, before the generation of the computed tomography exposure, an image known as a topogram is typically generated by means of x-rays as an overview exposure in the framework of the examination planning. For the generation of the topogram, the patient is located in a defined position while a gantry (carrying an x-ray source as well as an associated detector device) of the computed tomography apparatus is located at an established angular alignment. The gantry that rotates during a computed tomography acquisition must therefore be braked to the point of a stop before the generation of the topogram. Due to the typical rotation speed of the gantry of up to three revolutions per second and a mass of the gantry on the order of one metric ton, this entails a significant time expenditure of, for example, approximately one minute. The same time expenditure is incurred in order to accelerate the gantry to the original rotation speed again after the generation of the topogram. Furthermore, an unavoidable radiation exposure of the patient is associated with the generation of the topogram.

SUMMARY OF THE INVENTION

An object of the present invention is to enable operation of an imaging apparatus with particularly low exposure (in particular radiation exposure) for the patient.

The above object is achieved in accordance with the present invention in an imaging apparatus having an examination space in which a region of an examination subject to be examined can be positioned, and having an optical image acquisition sensor that acquires an optical image of a surface of the examination subject in the examination space. An evaluation unit generates control information from surface data of the subject obtained from the optical image, the control information being used to control an image data acquisition unit of the apparatus. The evaluation unit has access to a memory, in which the surface data are stored correlated with information acquired by the image data acquisition unit.

The inventive apparatus enables the acquisition of structures inside the examination subject, in particular the acquisition of a slice exposure of the examination subject, so that in principle a computed tomography modality operating with x-ray radiation as well as a magnetic resonance modality can be used. Computed tomography represents the preferred application field of the invention.

In addition to the (advantageously x-ray-related) transmission and detection devices of the imaging apparatus, it includes an optical image acquisition sensor that acquires an optical image of the surface of the examination subject in the examination space. The optical image acquisition sensor is arranged such that it enables a surface image acquisition of the examination subject when the subject is located in the same position as for a radiographic examination using the diagnosis unit (in particular an x-ray radiator and detector unit) of the imaging apparatus.

For linking the optical image acquisition sensor with the imaging diagnosis unit with regard to data therefrom, an evaluation unit is provided that makes the acquired surface data of the examination subject (in particular patients) usable as control information for activation of the imaging diagnosis unit. An automatic adoption of data acquired by means of the optical image acquisition sensor into an examination protocol of the imaging apparatus is provided, the examination protocol establishing the workflow of the radiographic examination. The surface data acquired by the optical image acquisition sensor are stored correlated with volume information acquired by means of the imaging diagnosis unit.

The optical acquisition of the position of the patient while the patient is located in the same position as for the computed tomography examination minimizes the risk of a mis-positioning of the patient as well as the risk of misinterpretation diagnostic data This is particularly the case for special examinations, for example of the hand, in which the arm is extended above the head of the patient and the image acquisition is implemented contrary to the otherwise-typical convention in radiology, which assumes a viewing direction from below through the patient.

Due to the correlated (and thereby logically linked) storage of the surface data acquired by the optical image acquisition sensor with the volume information acquired by the diagnosis unit, this linked information is also available for further purposes, such as for navigation purposes in medical interventions.

Various advantages result from the possibility to display information at a display device (the information having been acquired by the imaging diagnosis unit (in particular an x-ray radiator and detector device)) in correlation with data that have been acquired with the optical image acquisition sensor. The display device (for example a screen of the computed tomography apparatus also used in the examination planning) advantageously enables a representation of the surface of the examination subject in real time. A real time representation means a screen representation for which (unavoidable) delays (dependent on the system) are so slight in relation to the acquired subject matter that an observer detects no time offset of the screen display.

The surface of the examination subject acquired by means of the optical image acquisition sensor preferably is represented in three-dimensional form, in particular bordered or as a grid. Furthermore, the evaluation unit can enable a shift as well as an enlargement or shrinking of the surface region of the examination subject shown on the display device. In all types of representation of the surface, it can be shown in an advantageous manner together with regions to be examined (in particular slices) inside the examination subject.

The display, device, moreover offers the possibility to display an image or a representation of a surgical instrument simultaneously with a volume, section and/or surface representation of the examination subject. The images acquired by means of the imaging diagnosis unit as well as by means of the optical image acquisition sensor can then be used for navigation purposes in medical inventions.

In a preferred embodiment, a CMOS sensor that interacts with a pulsed laser beam as a light source is provided as the optical image acquisition sensor. The CMOS sensor acquires information from a number of individual light flashes. Independent of the embodiment of the image acquisition sensor, it is supported or mounted in a spatially variable manner (in particular pivotable relative to the examination subject) in the imaging apparatus.

An advantage of the invention is the dose reduction that is achieved in computed tomography examinations, this dose reduction being achieved by the combination of optical light methods for shape recognition with x-ray methods.

DESCRIPTION OF THE DRAWINGS

FIG. 1 schematically illustrates a cross-section through the data acquisition unit, and associated function blocks, of an imaging apparatus described for combined optical and x-ray diagnosis in accordance with the invention.

FIG. 2 is a flow chart of an examination using an imaging apparatus in accordance with the invention.

DESCRIPTION OF THE PREFERRED EMBODIMENTS

Figure 3:
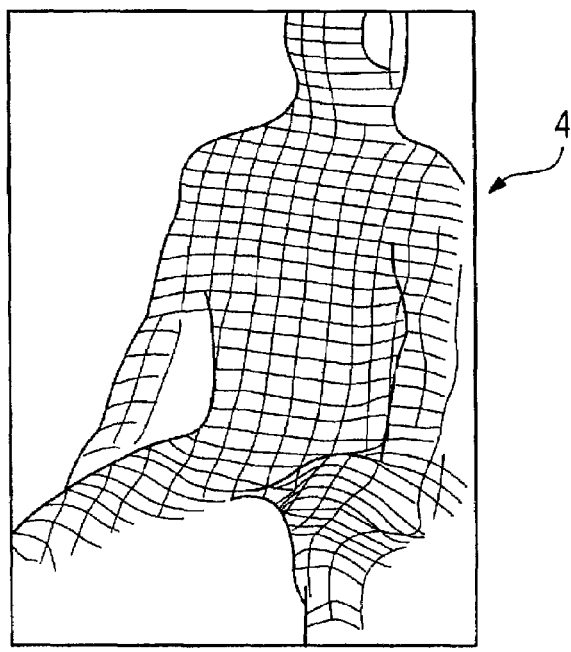
FIGS. 3 through 5 show examples of the representation of surfaces of an examination subject to be examined with the imaging apparatus according to the invention.

A gantry 2 that is rotatable around an axis perpendicular to the plane of the drawing is shown in FIG. 1 in a schematic section. The gantry is a component of an imaging apparatus 1, namely a computed tomography apparatus. A patient bed 3 on which the patient 4 is located is arranged within the circular cross-section of the gantry 2. The space within the cross-section of the gantry 2 above the patient bed 3, in which space the patient 4 is located, is designated as examination space 5. For optical monitoring of this examination space 5, a CMOS sensor is provided as an optical image acquisition sensor 6 that occupies a position defined relative to the gantry 2 as well as relative to the patient bed 3 and can be pivoted around the cited axis of the gantry 2 such that, for example, a 0° position (also designated as a 12:00 position), a +90° position (3:00 position) and a −90° position (9:00 position) can be set.

The image acquisition sensor 6 enables at least one portion of the surface of the examination subject (thus of the patient 5 to be examined) to be shown on a screen as a display device 7. The screen of the display device 7 is linked with an evaluation unit 8 which is embodied in a data processing system used for operation of the imaging apparatus 1. Both the image acquisition sensor 6, and an x-ray source 9 as well as an x-ray detector 10 that form an image data acquisition unit 11, are attached to the evaluation unit 8.

The evaluation unit 8 is designed (in particular in terms of software) such that a surface data acquired by the image acquisition sensor 6 can be used as control information for control of the image data acquisition unit. As used herein, "control" means any influencing of the operation of the image data acquisition unit. In particular the positioning and movement of the x-ray source 9 relative to the patient bed 3 is included as such control. In computed tomography examination of the patient 4 the patient bed 3 and/or one or more components 9, 10 of the image data acquisition unit can be moved. The computed tomography examination can be a spiral computed tomography examination.

In each case data that have been acquired with the aid of the optical image acquisition sensor 6 can be used for planning the computed tomography examination. According to the workflow of the preparation (shown simplified in FIG. 2) of an examination to be implemented with the imaging apparatus 1, a surface exposure of the appertaining region of the examination subject 4 is created with the image acquisition sensor 6 in a first step S1. In the next step S2, data acquired in the first step S1 are linked with further data relevant for the examination (in particular with patient data PD) in order to create an examination protocol UP based on this, according to which examination protocol UP the computed tomography examination is implemented with the apparatus 1. Data acquired in the step S1 are thereby automatically adopted into the examination protocol UP by means of the evaluation unit 8, which can also be realized in the form of a networked computer system.

The optical image acquisition sensor 6 enables a generation of three-dimensional surface data in cooperation with a light source 12 (such as a pulsed laser) which can also be integrated into the image acquisition sensor 6. FIG. 3 shows an example of a three-dimensional representation that can be generated by means of the image acquisition sensor 6. For illustration of the wide-ranging possibilities of the spatial representation, in FIG. 3 the patient 4 is shown sifting while in the imaging apparatus 1 he is typically located in a recumbent position.

The laser radiator 12 emits light pulses with a duration of less than 30 nanoseconds in the direction of the patient 4. Reflections of these pulses are acquired by the image acquisition sensor 6 (which has a semiconductor array of, for example, 1000 pixels). The diaphragm of the image acquisition sensor 6 is realized electronically and exhibits a suitably high switching frequency. The light intensity of individual pixels thus is detected, with which light intensity the distance of the appertaining subject points (meaning points on the surface o the examination subject 4) is detected. The image of the patient 4 shown in FIG. 3 is generated in real time with this measurement data by software in the evaluation unit 8. On the screen 7, the operator of the imaging apparatus 1 thus can track any variation of the positioning of the patient 4 relative to the image acquisition sensor 6.

The operator furthermore has the possibility to shift, zoom or manipulate in another manner the representation of a surface region of the patient 4 that is visible on the screen 7.

A memory 13, which can be part of the evaluation unit 8, is provided for storage of data, such as data that can be processed by the evaluation unit 8. This memory 13 enables the correlated storage of information determined with the image acquisition sensor 6, which information pertains to the surface of the examination subject 6, and information that has been acquired by the image data acquisition unit. This logically-linked storage of information acquired by means of optical light together with information acquired by computed tomography is also usable for further purposes, for example navigation purposes in medical interventions.

The acquisition of a surface of the examination subject 4 by the image acquisition sensor 6 integrated into the imaging apparatus 1 is in particular advantageous for routine applications in which conclusions about the position of internal structures of the examination subject 4 to be examined, which conclusions are sufficient for a computed tomography examination, can be made from the position of the acquired surface. The image acquisition sensor 6 (which can also be composed of a number of individual sensors) is suitable in an advantageous manner for implementation of video raster stereography (VRS) that, without any exposure with x-ray radiation, is based solely on surface information determined by optical light so as to substitute for a portion of the radiographic examination.

Figure 4:
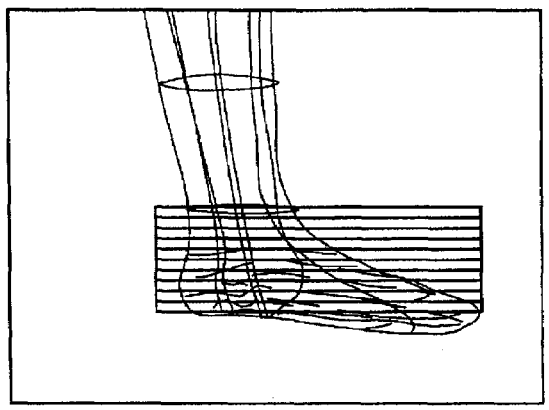
Figure 5:
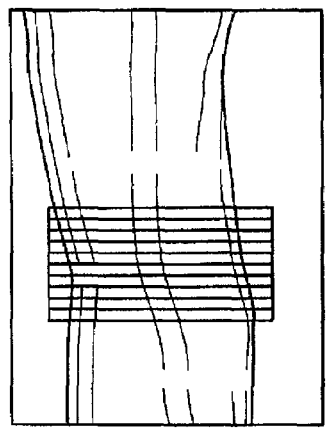

Application cases that pertain to orthopedic questions are illustrated in FIGS. 4 and 5, in these cases a surface grid shows a foot (FIG. 4) or a knee (FIG. 5) of the patient 4. In both cases the surface images acquired with the image acquisition sensor 6 are sufficient for the planning of a computed tomography examination, in particular for definition of slices (as shown in FIGS. 4 and 5) and/or of the examination volume. This also applies for the planning of a spiral CT examination.

Although modifications and changes may be suggested by those skilled in the art, it is the intention of the inventor to embody within the patent warranted hereon all changes and modifications as reasonably and properly come within the scope of his contribution to the art.

I claim:

1. An imaging apparatus comprising:
    an image data acquisition unit having an examination space in which a region of an examination subject is positionable, said image data acquisition unit being operable to acquire image data from the examination subject;
    an optical image acquisition unit mounted at a location relative to said image data acquisition unit to acquire an optical image of a exterior surface of the examination subject said optical image comprising surface data of the examination subject;
    a memory in which said surface data acquired by the optical image acquisition sensor are stored correlated with image data acquired by said image data acquisition unit;
    an evaluation unit having access to said memory that generates control information from said surface data for controlling said image data acquisition unit to acquire said image data; and
    said evaluation unit comprising a display device at which said optical image of the surface of the examination subject, acquired by said optical image acquisition sensor, is displayed.

2. An imaging apparatus as claimed in claim 1 wherein said image data acquisition unit is operable to generate an exposure of a slice of said region of the examination subject.

3. An imaging apparatus as claimed in claim 1 wherein said image data acquisition unit comprises an x-ray radiator and an x-ray detector to acquire x-ray image information as said image data.

4. An imaging apparatus as claimed in claim 3 comprising a rotatable gantry on which said x-ray radiator and said x-ray detector are mounted, said gantry being rotatable around said examination space.

5. An imaging apparatus as claimed in claim 1 wherein said image data acquisition unit is a magnetic resonance apparatus.

6. An imaging apparatus as claimed in claim 1 wherein said evaluation unit causes said display device to display said optical image of said examination subject in real time.

7. An imaging apparatus as claimed in claim 1 wherein said evaluation unit operates said display device to display said optical image of said surface as a grid.

8. An imaging apparatus as claimed in claim 1 wherein said evaluation unit is operable to allow displacement of said optical image of said surface of the examination subject at said display device.

9. An imaging apparatus as claimed in claim 1 wherein said evaluation unit is operable to allow variation of a size of said optical image of said surface of said examination subject at said display device.

10. An imaging apparatus as claimed in claim 1 wherein said evaluation unit causes said optical image of said surface of said examination subject to be displayed at said display device together with information representing an interior of the examination subject.

11. An imaging apparatus as claimed in claim 1 wherein said optical image acquisition sensor is a CMOS sensor.

12. An imaging apparatus as claimed in claim 1 wherein said optical image acquisition sensor is mounted so as to be movable relative to said examination subject.

13. An imaging apparatus as claimed in claim 1 comprising a light source operating in combination with said optical image acquisition sensor.

14. An imaging apparatus as claimed in claim 13 wherein said light source is a pulsed laser.

15. A method for adjusting operating parameters of an imaging apparatus, comprising the steps of:
    acquiring an optical image of an exterior surface of an examination subject located in an image data acquisition device;
    acquiring image data representing an interior of the examination subject from the examination subject using the image data acquisition device, with the examination subject located in said examination space;
    automatically electronically correlating surface data, represented by said optical image, with said image data representing an interior of the examination subject;
    automatically adjusting operating parameters of said image data acquisition unit, dependent on said surface data, to properly position an internal region of the examination subject relative to the image data acquisition apparatus for obtaining said image data representing an interior of the examination subject; and
    visually displaying said optical image of the surface of the examination subject.

* * * * *